United States Patent [19]

Hoet et al.

[11] Patent Number: 5,385,824
[45] Date of Patent: Jan. 31, 1995

[54] METHOD FOR DETECTION OF ANTI-RNA-ANTIBODIES

[75] Inventors: Rene M. A. Hoet, Cambridge, Great Britain; Waltherus J. Van Venrooy, Nijmegen, Netherlands

[73] Assignee: Akzo N.V., Arnhem, Netherlands

[21] Appl. No.: 90,147

[22] PCT Filed: Jan. 16, 1992

[86] PCT No.: PCT/EP92/00106
§ 371 Date: Sep. 20, 1993
§ 102(e) Date: Sep. 20, 1993

[87] PCT Pub. No.: WO90/10229
PCT Pub. Date: Sep. 7, 1990

[30] Foreign Application Priority Data

Jan. 22, 1991 [EP] European Pat. Off. ............ 91200121

[51] Int. Cl.$^6$ ................ G01N 33/537; G01N 33/543; G01N 33/564
[52] U.S. Cl. ............................. 435/6; 435/7.95; 436/506; 436/508; 436/518; 436/538
[58] Field of Search ................ 435/6, 7.95; 436/506, 436/508, 518, 538

[56] References Cited

U.S. PATENT DOCUMENTS 4,784,942 11/1988 Harley ..................... 435/7

FOREIGN PATENT DOCUMENTS 9010229 9/1990 WIPO .

OTHER PUBLICATIONS

D. Eliat et al, *Jour. Immunol.*, 120, 550–557, 1978.
Gioud et al., "Etude des anticorps antihistones et anti--ARN bicatenaires dans les connectivites par une technique immunoenzymatique," Revue Du Rhumatisme, vol. 49, No. 5, pp. 385–391, Apr. 1982, Paris, France.
Adamashvili et al., "Antibodies to nucleic acids in systemic lupus erythematosus and rheumatoid arthritis patients and their relatives," Immunology Letters, vol. 6, pp. 33–38, 1983.
Deutscher et al., "A sequence-specific conformational epitope on U1 RNA is recognized by a unique autoantibody,"Proceedings of the National Academy of Sciences, vol. 85, No. 10, pp. 3299–3303, May 1988, USA.
Wilusz et al., "Autoantibodies specific for U1 RNA and initiatior methionine tRNA,"The Journal of Biological Chemistry, vol. 261, No. 12, pp. 5467–5472, Apr. 25, 1986, USA.
Pesce et al., "Use of enzyme-linked antibodies to measure serum anti-DNA antibody in systemic lupus erythematosus," Clinical Chemistry, vol. 20, No. 3, pp. 353–359, Mar. 1974.

*Primary Examiner*—David Saunders
*Attorney, Agent, or Firm*—William M. Blackstone

[57] ABSTRACT

Method for monitoring patients having connective tissue autoimmune diseases comprising contacting patient specimens with (U1)RNA and detecting immune complexes formed, the level of reaction indicating the severity of the disease.

9 Claims, 1 Drawing Sheet

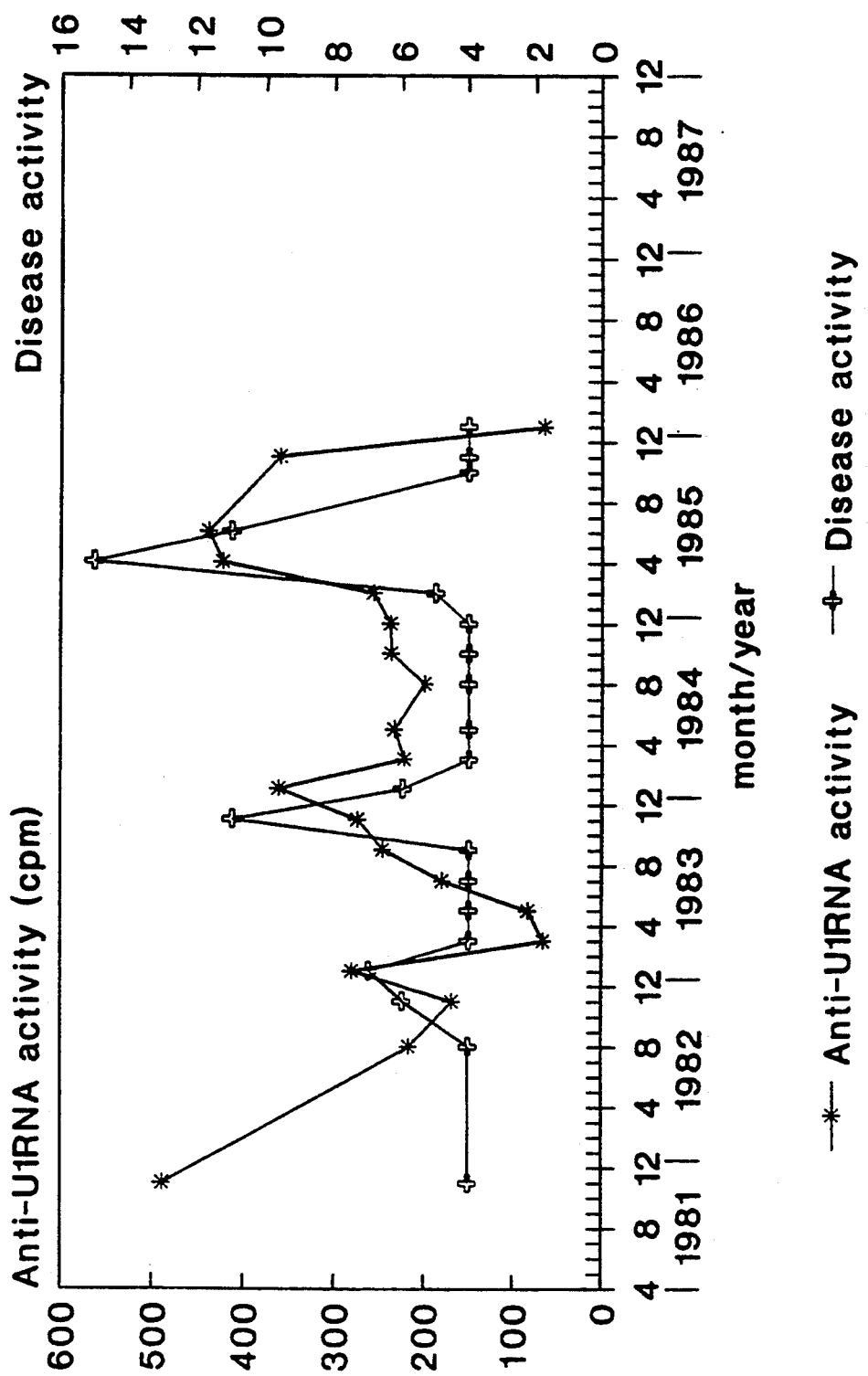

METHOD FOR DETECTION OF ANTI-RNA-ANTIBODIES

The invention relates to a method for monitoring an autoimmune disease activity by detection and quantitative determination of anti-RNA antibodies in a test fluid of patients with an autoimmune disease and a test kit for carrying out the method.

BACKGROUND OF THE INVENTION

Since the discovery that sera of patients with systemic lupus erythematosus (SLE) contain antibodies to nuclear components, more refined methods have been developed to define the antigens involved in the reaction and to measure the concentration of antibody. Methods used to establish the nature of the antigen and antibody have included complement fixation, hemagglutination, precipitation of soluble immune complexes with ammonium sulfate, immunoprecipitation by double diffusion in agar and immunohistology. The reaction has been quantitated by dilution of the sera for immunohistology, by the extent of binding of DNA by the sera, and by solid phase radio immunoassay. The use of antibodies coupled to enzymes has opened the possibility of using such conjugates to replace the radioactive label in immunoassay systems.

Pesce et al (Clinical Chem. 20/3, 353–359, 1974) described a technique consisting of preparing an antigen on an insoluble support, layering the test serum with anti-DNA, and using this serum as an antigen to react with an anti-human IgG labeled with enzyme-peroxidase. In principle, the amount of IgG bound to the insoluble support is proportional to the amount of antibody contained in the serum. Pesce et al demonstrated that a solid phase noncompetitive binding assay, with use of a second antibody conjugated to an enzyme as the quantitive or detector system, is a valid way to measure antibody to DNA in serum.

Patients with systemic autoimmune diseases produce a variety of antibodies directed against normal cellular components. Several well characterized autoantibody systems are directed against specific proteins or nucleic acid-protein complexes (Tan, E. M (1989) Adv. Immunol. 44, 93–151). Sera from patients with connective tissue diseases often contain antibodies against cellular components consisting of proteins associated with small RNA molecules of 80–200 nucleotides in length. Autoantibodies against the nuclear type of these small RNA-protein complexes (snRNP) are mostly found in sera from patients with SLE or SLE overlap syndromes. Several specificities have already been described. There are antibodies that precipitate (U1)snRNP only, due to the fact that they recognise one or more of the (U1)snRNP specific proteins viz. 70K, A and C. Another specificity, anti-Sm, precipitates all the major nucleoplasmic snRNPS due to the fact that these antibodies recognise the proteins B'/B and D which are common to these snRNPS (v. Venrooij and Sillekens, Clin. Exp. Rheum., 1989).

The antibodies in the patients sera are in all these cases directed against proteins contained in the snRNP complexes. Although nucleic acids are generally poor immunogens, autoantibodies directed against nucleic acids have been reported. The majority of studies of nucleic acid antibodies have concerned anti-DNA activities, although examples of anti-viral RNA autoantibodies have been described.

Antibodies against the (U)RNA components of snRNP are thought to be rare (Tan, 1989). Wilusz and Keene described in 1986 (J. Biol. Chem. 261, 5467–5472) the presence of anti-(U1)RNA autoantibodies in two anti-RNP sera. From this article no general conclusions regarding an association between anti-RNP and/or Sm activity and anti-(U1)RNA activity could be drawn. Deutscher and Keene described in 1988 (P.N.A.S., 85, 3299–3303) that the part of the (U1)-RNA recognised by one of said sera was mapped and found to include the second stem-loop of the RNA.

We initiated a study in which a large number of anti-snRNP sera were tested for the presence of anti(U1)-RNA antibodies. Via screening with CIE (counter immuno-electrophoresis) and IB (immunoblotting), 118 sera containing anti-snRNP activity were identified. Following RNP immunoprecipitation sixty sera were classified as anti-(U1)RNP and 18 sera as anti-Sm. Twenty-five sera contained anti-RNP as well as anti-Sm antibodies while 15 sera exhibited anti-(U1,U2)RNP activity.

These 118 sera were all tested for their ability to precipitate de-proteinized (U)RNA's. For this purpose total 32P labeled Hela cell RNA, purified by extensive pronase and phenol/detergent treatment, but also in vitro synthesized (U)RNA's, was used as antigen in the precipitation assay. Immunoprecipitation was carried out in IPP/500 mM NaCl, 10 mM Tris pH 7,5 and 0.05% Nonidet P40(R). The overall results show that 45 out of the 118 sera (about 40%) contained anti-(U1)snRNA antibodies. These antibodies were not present in the anti-Sm sera. The autoantibodies were always directed against (U1)snRNA and are most often present in patients with SLE overlap syndromes. Using immunoprecipitation under stringent conditions (500 mM NaCl) with in vitro synthesized (U1)RNA or in vivo labeled total Hela cell RNA, it has been found that about 65% of the SLE overlap syndrome and about 30% of the SLE sera with anti-snRNP activity contained antibody against (U1)RNA. No autoantibodies against other (U)RNAs were detected. Using in vitro synthesized stem-loops of (U1)RNA, it is possible to detect antibodies against all individual stem-loops of (U1)RNA. The major antigenic regions are however located in the so-called second (the B) and fourth (the E) stem-loop domain of (U1)RNA. It appears that the nucleotide sequence UUCG (nrs. 150–154) in the fourth E-stem loop is extremely essential as recognition site by patient specific antibodies.

The correlation between anti-(U1)RNA antibody level and autoimmune disease activity was most surprising.

BRIEF DESCRIPTION OF THE INVENTION

According to the invention anti-RNA antibodies can be detected in a test fluid by contacting RNA with said test fluid by which a reaction occurs between the RNA and anti-RNA antibodies present in the test fluid after which a determination of the antibodies reacting with the RNA may indicate and predict a change in the severity of disease.

Preferably above-mentioned determination of the antibodies reacting with the RNA will be a quantitative determination of the number of antibodies reacting with the U1RNA indicating a change in the severity of the disease.

The method according to the invention can be used to detect anti-(U1)RNA antibodies in serum from patients with the autoimmune disease SLE or SLE overlap syndrome.

In order to perform the method according to the invention the RNA used is preferably labeled RNA, for instance labeled with a radioactive isotope or with biotin. However RNA attached to a solid phase like the innerwall of a microtiter plate is also an option in order to perform the method.

Part of the invention is also a test kit for carrying out the method according to the invention.

BRIEF DESCRIPTION OF THE FIGURES

FIG. 1 is a graph showing the correlation of anti-U1 RNA antibodies in serum with disease activity.

DETAILED DESCRIPTION OF THE INVENTION

The invention will be explained in more detail below. Using a rapid and quantitative dot-blot binding assay as described below the correlation between disease activity and level of anti-(U1)RNA antibodies is demonstrated and outlined in FIG. 1. In said FIG. 1 is depicted that anti-(U1)RNA activity is predominantly found in patients with active disease. A typical dot-blot binding assay can be performed as follows. The labeled (U1)-RNA transcript is made in vitro using T7 polymerase and (U1)cDNA. The RNA can be labeled in various ways (radioactive, with biotin etc.). The labeled RNA is incubated under certain conditions and in a buffer with diluted test fluid from patients (serum, plasma etc.). The patient antibodies are able to bind the (U1)RNA and after equilibration has been reached (1 hr) the mixture is sucked off through a nitrocellulose sheet in a dot blot apparatus, using for example the Schleicher and Schull manifold with 96 wells. Under test conditions, while naked RNA will not bind to the NC sheet, an RNA-antibody complex will. The NC sheet is washed, dried and detection of the labeled RNA bound on the NC via the antibody can be carried out, qualitatively and quantitatively. It is extremely important that the (U1)RNA offered to the test fluid is present in excess in order to obtain a linear correlation between concentration of antibody and amount of (U1)RNA bound. The method can also be performed using individual domains or epitopic regions of the (U1)RNA. This is important because in certain sera the severity of disease might correlate only with one class of antibody directed against only one epitopic region. In a three year prospective study disease activity indexes and levels of antibody activity against (U1)RNA were measured. Surprisingly, major disease exacerbations are associated with an increase of anti-(U1)RNA titer. This has now been found in more than 10 patients which were followed for 3 years or more. Strikingly, in the same patients no correlation between disease activity and antibody levels against the RNP-proteins (70K and A) could be found. By measuring the level of anti-(U1)RNA activity according to the invention it is now for the first time possible to monitor the disease activity and predict disease exacerbations which is extremely important for the assessment of the disease. By using the method according to the invention a physician is able to predict to a certain extent that the patient will evolve into a weaker condition. With this knowledge the physician can prescribe at the right moment certain medicaments that will bring the patient into a better condition or prevent a worsening of the disease.

According to the invention the method can also be performed using RNA attached to a solid phase. For such a purpose the wall of a small well in a microtitration plate to which said RNA is bound has often been used. The test fluid to be investigated is introduced in the small wells of the microtitration plate. The bound RNA is able to react with antibodies, specifically with anti-(U1)RNA antibodies, present in the serum from patients with SLE or MCTD syndrome as a result of which said anti-(U1)RNA antibodies are bound. In order to be able to detect whether an immunochemical reaction has taken place, subsequently one can use for instance marked antibodies which are directed against the autoantibodies to be determined. Said marked antibodies will react with the RNA-auto antibody complex formed already on the solid phase. The marked antibodies consist of antibodies to which an enzyme is bound, preferably a peroxidase-enzyme. In the next step, a colourless solution (substrate+chromogen) is added. The enzyme is able to convert this solution into a coloured compound.

The intensity of the colour depends on the quantity of enzyme which is proportional to the quantity of bound autoantibody. Said colour can be altered by adding a stop reagent.

The method thus described of determining an autoantibody in the test fluid is a method of the sandwich type. Other immunochemical methods, such as an agglutination, inhibition or a competition reaction, can also be used. As suitable enzymes one can use, inter alia, alkaline phosphatase, urease and a previously mentioned peroxidase, preferably Horse Radish Peroxidase (HRP).

Instead of the above-mentioned wall of a small well in a microtitration plate as solid phase one can use a tube or capillary, a membrane, filter, teststrip or the surface of a particle such as, for example, a latex particle, an erythrocyte, a dye sol, a metal sol or metal compound as sol particle.

Instead of above-mentioned enzymes as marker one can use as labelling substances, inter alia, a radioactive isotope, a fluorescent compound, a dye sol, metal sol or metal compound as sol particle.

In the claims:

1. A method for monitoring a patient having connective tissue autoimmune disease comprising contacting (U1)RNA with a fluid specimen from the patient and determining whether an immune complex has formed between the (U1)RNA and any antibodies present in the specimen, wherein the level of reaction with the (U1)-RNA correlates with connective tissue autoimmune disease activity.

2. A method according to claim 1, wherein the determination of antibodies reacting with the (U1)RNA is a quantitative determination of the level of reaction with the (U1)RNA.

3. A method according to claim 2, wherein the anti-(U1)RNA reactive antibodies are immunoreactive with RNA containing the B stem-loop domain of (U1) RNA.

4. A method according to claim 2, wherein the anti-(U1)RNA reactive antibodies are immunoreactive with RNA containing the E stem-loop domain of (U1)RNA.

5. A method according to claim 2, wherein the (U1)-RNA is labeled (U1)RNA.

6. A method according to claim 2, wherein the (U1)-RNA is attached to a solid phase.

7. A method according to claim 1, wherein the fluid specimen is serum, plasma or blood.

8. A method according to claim 7, wherein the fluid specimen is from patients with an autoimmune connective tissue disease selected from the group consisting of systemic lupus erythematosus or systemic lupus erythematosus-overlap syndrome.

9. A test kit for performing a method for monitoring a patient having connective tissue autoimmune disease, comprising a solid phase coated with (U1)RNA and a container of labeled antibodies that react with anti-RNA antibodies from a fluid specimen that are immunoreactive with the (U1)RNA on the solid phase.

* * * * *